US012558373B1

(12) United States Patent　　　　　(10) Patent No.:　US 12,558,373 B1

Wanderer　　　　　　　　　　　　　(45) Date of Patent:　　Feb. 24, 2026

(54) METHOD FOR CONVERTING ATRIAL FIBRILLATION TO SINUS RHYTHM WITH LOW-RISK, LOW-COST PROTOCOL, AND PREVENTING RECURRENCE OF ATRIAL FIBRILLATION

(71) Applicant: Alan Wanderer, Bozeman, MT (US)

(72) Inventor: Alan Wanderer, Bozeman, MT (US)

( * ) Notice: Subject to any disclaimer, the term of this patent is extended or adjusted under 35 U.S.C. 154(b) by 0 days.

(21) Appl. No.: 18/906,805

(22) Filed: Oct. 4, 2024

(51) Int. Cl.
| | |
|---|---|
| *A61K 31/405* | (2006.01) |
| *A61K 9/00* | (2006.01) |
| *A61K 33/06* | (2006.01) |
| *A61P 9/00* | (2006.01) |

(52) U.S. Cl.
CPC ............ *A61K 33/06* (2013.01); *A61K 9/0053* (2013.01); *A61P 9/00* (2018.01)

(58) Field of Classification Search
None
See application file for complete search history.

(56) References Cited

U.S. PATENT DOCUMENTS 6,620,836 B1 * 9/2003 Patrick ................... A61K 45/06
514/415

OTHER PUBLICATIONS

Lutsey et al (A Pilot Randomized Trial of Oral Magnesium Supplementation on Supraventricular Arrhythmias. Nutrients 2018, 10, 884) (Year: 2018).*

Cacioppo et al (Association of Intravenous Potassium and Magnesium Administration With Spontaneous Conversion of Atrial Fibrillation and Atrial Flutter in the Emergency Department. JAMA Network Open. 2022;5(10) p. 1-11) (Year: 2022).*

Sanger (Are Bananas Good for Atrial Fibrillation? (2023)). (Year: 2023).*

* cited by examiner

*Primary Examiner* — Jake M Vu

(74) *Attorney, Agent, or Firm* — Collaborative IP; Paul Ditmyer

(57)　　　　　　　ABSTRACT

The method is for treating an individual having atrial fibrillation (AF) with administration of oral magnesium supplementation for converting atrial fibrillation to sinus rhythm. The method includes monitoring cardiac rhythms frequently (e.g. daily), importance of remaining hydrated, adding potassium if needed, and administering a dose of oral magnesium supplements for at least four to six weeks, for example. The method includes titrating the dose of magnesium supplements until conversion of atrial fibrillation to sinus rhythm, and additional titrating of the dose of magnesium supplements based upon recurrence of atrial fibrillation, until conversion of atrial fibrillation to sinus rhythm. Monitoring 'Heart Rate Variability" in certain circumstances may forecast the presence or recurrence of atrial fibrillation.

22 Claims, 1 Drawing Sheet

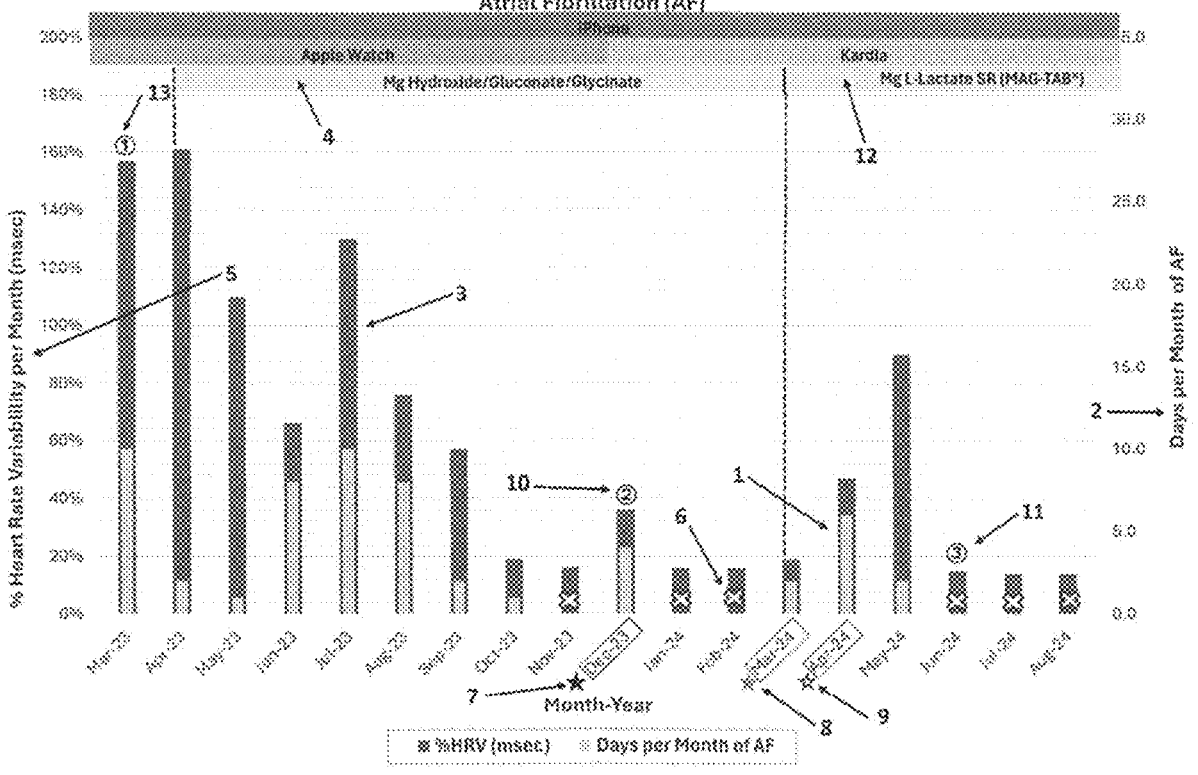

1

METHOD FOR CONVERTING ATRIAL FIBRILLATION TO SINUS RHYTHM WITH LOW-RISK, LOW-COST PROTOCOL, AND PREVENTING RECURRENCE OF ATRIAL FIBRILLATION

REFERENCES CITED

Joglar J A, Chung M K, Ambruster A L et al. 2023 ACC/AHA/ACCP/HRS Guideline for the Diagnosis and Management of Atrial Fibrillation: A Report of the American College of Cardiology/American Heart Association Joint Committee on Clinical Practice Guidelines. Circulation. 2024; 149: e 1-e156.

Hindricks G, Potpara T, Dagres N. et al; ESC Scientific Document Group. 2020 ESC Guidelines for the diagnosis and management of atrial fibrillation developed in collaboration with the European Association for Cardio-Thoracic Surgery (EACTS): the task force for the diagnosis and management of atrial fibrillation of the European Society of Cardiology (ESC) developed with the special contribution of the European Heart Rhythm Association (EHRA) of the ESC. Eur Heart J. 2021; 42:373-498.

Khan A M, Lubitz S A, Sullivan L M. et. al. Low serum magnesium and the development of atrial fibrillation in the community: the Framingham Heart Study. Circulation 2013 Jan. 1; 127(1):33-8. Markovits, N, Kurnik, D., Halkin, H, et. al, Database evaluation of the association between serum magnesium levels and the risk of atrial fibrillation in the community. Int. J. Cardiol. 2016, 205, 142-146

Misialek J R, Lopez F L, Lutsey P, et. al. Serum and dietary magnesium and incidence of atrial fibrillation in whites and in African Americans—Atherosclerosis Risk in Communities (ARIC) study. Circ J, 2013; 77(2):323-9

Shah S A, Clyne C A, Henyan N, et. al. The impact of magnesium sulfate on serum magnesium concentrations and intracellular electrolyte concentrations among patients undergoing radiofrequency catheter ablation. Conn Med 2008; 72:261-265.

McBride B F, Min B, Kluger J, et al: An evaluation of the impact of oral magnesium lactate on the corrected Q T interval of patients receiving sotalol or dofetilide to prevent atrial or ventricular tachyarrhythmia recurrence. Ann Non-inv Electro Cardiol 2006; 11:163-9.

Avioli L, Berman M. Mg28 kinetics in man. Journal of Applied Physiology. 1966; 21:1688-1694.

Elin R J. Magnesium metabolism in health and disease. Dis Mon. 1988; 34:161-218.

Zhang X, Gobbo, L C D, Hruby A, et. al. The Circulating Concentration and 24-h Urine Excretion of Magnesium Dose- and Time-Dependently Respond to Oral Magnesium Supplementation in a Meta-Analysis of Randomized Controlled Trials. J Nutra. 2016; 146:595-602.

Biesenbach P, Martensson J, Lucchetta L, et. al. Pharmacokinetics of magnesium bolus therapy in cardiothoracic surgery. J Cardiothorac Vase Anesth 2018, 32:11289-1294.

Adderley N, Niranthakumar K, Marshal T. Risk of stroke and transient ischaemic attack in patients with a diagnosis of resolved atrial fibrillation: retrospective cohort studies. BMJ 2018; 360: k1717.

Chuda A, Kaszkowiak M, Banach M, et. al. The relationship of dehydration and body mass index with the occurrence of atrial fibrillation in heart failure patients. Front Cardiovasc Med. 2021, 8:668653.

Krijthe B P, Heeringa J, Kors J A, et al. Serum potassium levels and the risk of atrial fibrillation: the Rotterdam Study. Int J Cardiol. 2013; 168(6):5411-5415. doi: 10.1016/j.ijcard.2013.08.04.

Nielsen F H, Milne D B, Klevay L M, et. al. Dietary magnesium deficiency induces heart rhythm changes, impairs glucose tolerance, and decreases serum cholesterol in postmenopausal women. J Am Coll Nutr. 2007; 26:121-132.

Sultan A, Steven D, Rostock T, et al. Intravenous administration of magnesium and potassium solution lowers energy levels and increases success rates electrically cardioverting atrial fibrillation. J Cardiovasc Electrophysiol.2012; 23(1):54-9.

Kotecha D. Magnesium for Atrial Fibrillation, Myth or Magic? Circ Arrhythm Electrophysiol. 2016; 9: e004521.

Dogteroma P, Fua C, Legga T, Chioua Y, et. al. The absolute bioavailability and the effect of food on a new magnesium lactate dihydrate extended-release caplet in healthy subjects. Drug Dev Ind Pharm. 2018, 44:1481-1487

Graber F; Bioavailability of US Commercial magnesium preparations, Magnes Res. 2001; 14:257-62.

Baker W L. Treating arrhythmias with adjunctive magnesium: identifying future research directions. Eur Heart J Cardiovasc Pharmacother. 2017; 3:108-117.

Spencer H, Norris C, Williams D. Inhibitory effects of zinc on magnesium balance and magnesium absorption. J Am Coll Nutr. 1994; 13:479-84.

Fine F D, Santa Ana C A, Porter J L, et. al. Intestinal Absorption of Magnesium from Food and Supplements. J Clin Invest. 1991; 88:396-402.

Verma A, Haines D E, Boersma L V et. al. Pulsed Field Ablation for the Treatment of Atrial Fibrillation: PULSED AF Pivotal Trial. Circulation. 2023; 147:1422-1432.

Kim S H, Lim K R, Seo J H, et al. Higher heart rate variability as a predictor of atrial fibrillation in patients with hypertension. Sci Rep. 2022 Mar. 8; 12:3702

Seaborn GEJ, Todd K, Michael K A, et. al. Heart Rate Variability and Procedural Outcome in Catheter Ablation for Atrial Fibrillation. Ann Noninvasive Electrocardiol 2014; 19(1):23-33

Broux B, De Clercq A., Decloedt A. Heart rate variability parameters in horses distinguish atrial fibrillation from sinus rhythm before and after successful electrical cardioversion. Equine Vet 2017; 49:723-728.

Abbreviations (1) AF=atrial fibrillation; (2) SR=sinus rhythm; (3) AFL-atrial flutter; (4) Mg=magnesium; (5) K=potassium; (6) Sodium=Na; (7) Calcium=Ca; (8) HCP=health care professional.

FIELD OF THE INVENTION

The present invention relates to a low-risk, low-cost treatment protocol for converting AF to SR. The treatment emphasizes the long-term administration of oral Mg supplements in combination with other elements in the protocol.

BACKGROUND

AF is defined as an irregular heart rhythm, medically referred to as an arrhythmia. AF rhythm is caused by erratic, chaotic electrical impulses in the heart, which leads to an irregular heart rhythm. During AF, the heart rate may be in the normal range or rapid (more than 100 beats per minute).

It is considered a lifetime chronic condition that may be asymptomatic and progress to severe symptomatology. Based on 2023 statistics from the *American College of Cardiology* 2023 *Practice Guidelines for AF* (Joglar J A, Chung M K, Ambruster et. al . . . 2023 Circulation. 2024; 149: e 1-e156), it affects approximately five to six million people in the United States and fifty million globally. The incidence is increasing because of an aging population, individuals not addressing predisposing risk factors for AF (i.e., obesity, excessive alcohol, smoking, sleep apnea, dehydration, excessive caffeine, aspartame sweeteners, and more), and increased detection. It is projected to increase to thirteen million in the USA by 2030. AF is one of the most common causes of strokes and has received considerable attention from medical and surgical professionals to find new, effective treatment options. The *American College of Cardiology* 2023 *Practice Guidelines for AF* (Joglar J A, Chung M K, Ambruster et. al . . . 2023 Circulation. 2024; 149: e 1-e156) indicates AF is associated with "a 1.5-to 2-fold increased risk of death; 2.4-fold risk of stroke; 1.5-fold risk of cognitive impairment or dementia; 1.5-fold risk of myocardial infarction (i.e., heart attack); 2-fold risk of sudden cardiac death; 5-fold risk of heart failure; 1.6-fold risk of chronic kidney disease; and 1.3-fold risk of peripheral artery disease. In Medicare beneficiaries, the most frequent outcome in the 5 years after AF diagnosis was death (19.5% at 1 year; 48.8% at 5 years); the next most common diagnosis was heart failure (13.7%), followed by new-onset stroke (7.1%), gastrointestinal hemorrhage (5.7%), and myocardial infarction (3.9%). AF's association with serious outcomes, particularly increased stroke risk, has garnered considerable attention from medical and surgical professionals to discover effective, new treatment options.

It is estimated fifty to eighty-seven percent of individuals with AF are initially asymptomatic, referred to as subclinical AF. The *American College of Cardiology* 2023 *Practice Guidelines for AF* (Joglar J A, Chung M K, Ambruster et. al . . . 2023 Circulation. 2024; 149: e 1-e156) has defined the following categories for AF: (1) subclinical AF is AF without symptoms, previously called asymptomatic; (2) first detected AF is the first documentation of AF regardless of previous symptoms; (3) paroxysmal AF is intermittent and originates and terminates within seven days; (4) persistent AF exists for more than seven days up to one year; (5) long-standing persistent AF exists for more than one year; and (6) permanent AF is when the individual with AF and the clinician stop further attempts to restore and/or maintain SR.

Symptoms associated with AF include palpitations, rapid heart rate, dizziness, fainting, chest pain, shortness of breath, excessive fatigue, and confusion. Symptoms of fatigue and confusion may be attributed to other conditions and delay the diagnosis of AF. Paradoxically, there is a greater chance of experiencing a stroke if you are asymptomatic versus having heart palpitations because palpitations may encourage earlier medical intervention. When diagnosed with asymptomatic or symptomatic AF, even on an anticoagulant, there remains a higher risk of experiencing a stroke compared to someone in SR (Adderley N, Niranthakumar K, Marshal T. BMJ 2018; 360:k1717.).

There are several conventional therapeutic interventions available to convert AF to SR. The most common involves medications to control heart rate and rhythm. Some of these medications have significant side effects or may not be permanently effective. Another option is electrical cardioversion, which delivers quick, low-energy shocks to the chest. This may work immediately but may not be permanent. Implantation of a pacemaker to regulate heart rate and rhythm is another treatment option. Last are surgical procedures.: (1) Cardiac catheter ablation involves threading a catheter into a leg vein up into the right upper chamber (right atrium) of the heart, through a wall (septum) into the left upper chamber (left atrium) where the erratic electrical impulses reside. The cardiologist, an electrophysiologist, maps the heart for locations of abnormal electrical impulses causing AF. Once identified, heat from radiofrequency probes or cold by cryotherapy will destroy the causative heart tissue, eliminating the chaotic, irregular electrical impulses. A new type of cardiac ablation, pulsed-field ablation, apparently makes AF-causing cells inactive and significantly reduces complications (Verma A, Haines D E, Boersma L V et. al. Circulation. 2023; 147:1422-1432). (;(2) The Cox-maze IV procedure is a more invasive open-heart procedure involving maze-like ablations to create scar tissue that blocks the abnormal electrical circuits causing AF; (3) A less invasive maze procedure uses thoracoscopy, a tube with a small camera. A small incision is made between the ribs, and the thoracoscope is inserted with other instruments to ablate the tissues causing AF. The surgeon may remove or close off a small section of the left upper heart chamber where clots form, reducing the risk of dislodging clots that cause strokes. Cardiac catheter ablation has become a common treatment for AF. Repeat cardiac ablation may be necessary to maintain SR.

These therapeutic interventions have varying success rates and require occasional repeat procedures for AF recurrences. Moreover, although they have been characterized as low risk, that conclusion is only valid if no serious complications occur. There is a litany of serious complications depending on the intervention. Examples of complications for each class of intervention include (1) Chemical cardioversion with antiarrhythmic medications can be associated with new or life-threatening arrhythmias; (2) Electrical cardioversion can dislodge a heart clot and cause a stroke; and (3) Cardiac ablation procedures can cause bleeding, blood vessel damage, dislodged blood clots causing a stroke and death.

The longer AF exists, the less effective conventional interventions are in converting AF to SR. Structural changes can occur over time in the heart, making it difficult for AF individuals to convert successfully to SR. Individuals diagnosed with asymptomatic AF are often on an anticoagulant to reduce stroke risk. However, there is still a higher risk for stroke in asymptomatic AF compared to individuals who are always in SR.

The heart requires four electrolytes (Na, K, Mg, and Ca) to initiate and conduct electrical impulses throughout the heart. Complex mechanisms involve selective pumping of each electrolyte into and out of heart cells. In particular, Mg must be retained in adequate concentrations inside heart cells to help generate electrical impulses in the pacemaker and to control heart rate by delaying electrical impulses in the middle of the heart. The movement of these electrolytes in and out of heart cells requires energy derived from a readily available molecule (ATP) that stores energy. ATPase is an enzyme that cleaves ATP, thereby releasing energy needed for cellular functions. This particular enzyme and ATP require Mg for optimal cleavage of ATP. Similar enzymes also require Mg to manufacture ATP. Mg is essential to provide energy for heart cells to function efficiently. Without adequate energy, heart cells in the pacemaker may fail, causing AF. Other electrolytes are also crucial for the efficient functioning of heart cells. Na is involved in electrical impulse generation and maintains water volume/pressure inside cells to prevent them from dehydrating. Ca initiates the contraction of heart cells, culminating in heartbeats. K is an essential mineral that must be maintained in critical concentrations inside heart cells, allowing pacemaker heart cells to rest before discharging sequential electrical impulses.

Following are summaries of studies that provide evidence Mg and/or K deficiencies predispose to AF. Summary (Khan A M, Lubitz S A, Sullivan L M. et. al. Circulation 2013 Jan. 1; 127(1):33-8.): The Framingham Heart Study involved long-term studies of Framingham, Massachusetts residents to observe heart disease epidemiology. The study included 3530 participants without history or physical evidence of any pre-existing cardiovascular disease. They had periodic cardiac evaluations over 20 years, and of the 3520 participants, 228 developed AF. Within this group of AF, eighty participants (thirty-five percent) had the lowest serum Mg levels, suggesting a positive correlation between low serum Mg and the development of AF. Subjects with the lowest Mg levels had a fifty percent increased risk of AF compared to participants with Mg levels in the upper limit. Summary (Nielsen F H, Milne D B, Klevay L M, et. al. J Am Coll Nutr. 2007; 26:121-132): The study involved fourteen post-menopausal women fed a Mg-restricted diet (thirty-three percent of the recommended daily allowance) for seventy-eight days. The participants resided in a research unit for the entire study to carefully monitor their Mg intake. During the low Mg diet phase, heart rhythm abnormalities appeared in five women, two of whom developed AF in combination with AFT; one had AFT and PVCs, two had PVCs, and one developed a heart block. The AF and AFT responded quickly with Mg supplementation. The participants with PVCs and heart block took longer to reverse with the Mg supplements. Summary (Markovits, N, Kurnik, D., Halkin, H, et. al, Int. J. Cardiol. 2016, 205, 142-146): 2228 participants without prior cardiovascular disease were followed over two years, and 162 developed AF. The data indicated a significant correlation between participants with the lowest serum Mg levels and an increased incidence of AF. Summary (Misialek J R, Lopez F L, et. al. Circ J, 2013; 77(2):323-9): 14,390 participants free of AF were studied over 20 years. AF was identified in 1,776 participants. They were divided into five groups depending on their serum Mg levels. The highest incidence of AF occurred in participants with the lowest serum Mg levels. The lowest incidence of AF occurred in individuals with average or higher Mg levels. Participants on diuretics also demonstrated a correlation between the lowest Mg levels and a higher risk of AF. Summary (Sultan A, Steven D, Rostock T, et al. J Cardiovasc Electrophysiol. 2012; 23(1):54-9). Electrical cardioversion was performed on 170 patients with persistent AF. Half the patients received intravenous solutions containing Mg and K during electrical cardioversion; the other half received a placebo. The group that received Mg/K had a significantly higher success rate of converting AF to SR than the placebo group. Additionally, the Mg/K group required less electrical energy to convert to SR than the placebo group. Summary (Krijthe B P, Heeringa J, Kors J A, et al., Int J Cardiol. 2013; 168(6):5411-5415. doi: 10.1016/j.ijcard.2013.08.04): The study population consisted of 4059 participants without AF. 474 developed AF over approximately 12 years. Low serum K levels were significantly correlated with a higher incidence of AF. Results were independent of age, sex, serum Mg levels, and other medically related variables.

The aforementioned studies provide strong evidence for the correlation between Mg and/or K deficiency and a predisposition to AF development. The following summaries include clinical studies that recognize AF-afflicted individuals can have Mg deficiency in their hearts even with normal serum Mg levels. Summary (Shah S A, Clyne C A, Henyan N, et al. Conn Med 2008; 72:261-265): Twenty-two AF patients undergoing catheter ablation received intravenous Mg sulfate or placebo. All patients had normal baseline Mg serum levels, and eighty-nine percent had a deficiency of Mg in their heart cells. Summary McBride B F, Min B, Kluger J, et al Ann Noninv Electro Cardiol 2006; 11:163-9.): AF patients on anti-arrhythmic medications had deficiencies in Mg concentrations inside their heart cells. Treatment with a long-acting oral Mg supplement normalized the Mg deficiency in heart cells and reduced the risk of fatal arrhythmias. Summary An overlooked fact is the blood compartment represents only one percent of the total body Mg stores (Elin R J. Dis Mon. 1988; 34:161-218). This has major clinical significance because a normal serum Mg level will not reflect low Mg concentrations in the heart cells of individuals with AF. In summary, these articles provide substantial evidence that AF-afflicted individuals frequently have normal Mg serum levels, which can be misleading since many have Mg deficiencies in their heart cells.

Studies have shown replenishing Mg stores occurs slowly over many weeks or months, The half-life of Mg is approximately one thousand hours, equating to forty-one days or six weeks (Avioli L, Berman M. Journal of Applied Physiology. 1966; 21:1688-1694.) The amount of Mg stored in humans is reduced by one-half every six weeks. Once Mg is absorbed, it is distributed and exchanged slowly between several anatomical compartments: blood, bones, muscles, and tissues. Consequently, Mg supplementation may require weeks to replenish Mg stores in the heart cells of AF-afflicted individuals. Assuming there is no pre-existing deficiency of Mg in the body and the amount of Mg absorbed and excreted are equal, it would require at least six weeks of the recommended daily allowance (RDA) for elemental Mg to maintain Mg body stores. If there is a pre-existing Mg deficiency, as in the heart cells of AF-afflicted individuals, it will take several half-lives of Mg to replenish and sustain Mg stores in the heart cells. In summary, Mg replenishment requires a long incubation time.

The correlation between Mg deficiency and AF does not always mean causality; consequently, significant medical literature indicates that Mg supplementation for AF conversion to SR is inconclusive. An editorial (Kotecha D. Circ Arrhythm Electrophysiol. 2016; 9: e004521) titled "Magnesium for Atrial Fibrillation, Myth or Magic?" concluded that intravenous Mg sulfate supplementation was inconclusive in converting or preventing AF. As previously mentioned, the half-life of Mg is six weeks, so consequently, it will take a long time for the Mg supplement to correct a deficiency of Mg in the body, especially in AF-afflicted individuals with Mg-deficient heart cells. Inconclusive treatment of AF with Mg sulfate infusions is likely a result of its short half-life of 12 hours (Biesenbach P, Martensson J, Lucchetta L, et al. J Cardiothorac Vase Anesth. 2018, 32:11289-1294) and that it is usually administered for only a few days.

Supporting the need to administer oral supplements for long durations is Mg pharmacokinetic data (Zhang X, Gobbo, L C D, Hruby A, et al. J Nutra. 2016; 146:595-602.) from studies administering oral Mg supplements to healthy subjects. The data was accumulated from 48 studies (meta-data analysis), and the results indicated oral Mg supplements required between 20 weeks (at 300 mg/day) to 30 weeks (at 400 mg/day) to achieve a steady state, i.e., achieving and maintaining maximal serum concentrations of Mg.

A few attempts have been made to prevent AF with oral Mg supplements. Participants for elective heart surgery (coronary artery bypass graft i.e., CABG) received oral Mg sulfate or a placebo for three days preoperatively and on the day of surgery (Tohme J, Sleilaty G, Jabbour K, et. al. Eur J Cardiothorac Surg. 2022:62: 1-8.). The Mg sulfate group significantly reduced post-operative AF compared to placebo. This study supports the potential benefit of oral Mg supplementation, but Mg sulfate was administered for only four days. It is not preferable for long-term administration because it has very poor bioavailability and may cause pronounced gastrointestinal side effects. Another study tested oral Mg hydroxide alone or in combination with an antiarrhythmic medication (sotalol) after electrical cardioversion to determine if Mg hydroxide alone or with sotalol reduced the post-cardioversion incidence of AF compared to placebo (Frick M, Darpo B, Ostergtren J, et al. Eur Heart J; 2000; 21:1177-1185). There was no difference in the recurrence rate of AF for Mg hydroxide with and without sotalol compared to placebo in patients monitored with periodic EKGs for up to 3 years. The design had serious inherent flaws because Mg hydroxide is poorly absorbed and is the main component in Milk of Magnesia, a very strong laxative.

A factor in choosing an oral Mg supplement may be the percentage of elemental Mg in each dose (tablet, capsule, etc.). Elemental Mg is the form of Mg that is essential for heart cells to function. The amount of elemental Mg in supplements is often not listed on the labels of Mg products.

Another consideration may be the absorption of magnesium. Based on several studies, organic magnesium supplements have the best absorption, which equates to more magnesium being distributed throughout the body (Graber F; Magnes Res. 2001; 14:257-62). It may be important to know whether the Mg supplement can achieve and maintain 24-hour blood levels. Most do not provide that data.

A slow-release Mg L-Lactate has data to support that one caplet has rapid absorption in the range of 40 percent and can obtain the C-max (maximum blood concentration) at a T-max (time of maximum blood concentration) by 10 hours. It can maintain Mg blood levels within the C-max range for 24-hour intervals (Dogterom P, Fu C, Legg T. Drug Dev Ind Pharm, 44:9, 1481-1487). Moreover, in patients with arrhythmias that included AF with preexisting low cardiac intracellular Mg concentrations, the intracellular Mg concentrations normalized over a 51-hour time span after administration of the same slow-release Mg L-Lactate supplement (McBride B, Min, B, Kluger, J et. al. Ann Noninvasive Electrocardiol. 2006; 11(2):163-169. In this same study, the aforementioned slow-release Mg L Lactate administered to these subjects showed a reduction in the QTc interval (electrical activity in the EKG interval) at one hour, which was maintained for 51 hours. This demonstrated that the supplement was rapidly absorbed, as evidenced by its one-hour effect on the electrical activity of the heart that lasted 51 hours, and simultaneously, this supplement normalized deficient Mg in heart cells over the same time span of 51 hours.

Optimal Mg supplements containing the highest elemental Mg content and the best absorption do not fulfill the daily elemental Mg RDA required for individuals with or without Mg deficiency. A similar recognition is for individuals needing K supplements. Consequently, a protocol that emphasizes the need for consumption of foods high in Mg and K content may be needed.

Adequate hydration is frequently advised to maintain good health and for many medical conditions. One study described the causal relationship between dehydration and AF. It noted the total water content was significantly diminished in AF-afflicted individuals who were older, had a higher BMI, and were on a diuretic for heart failure., (Chuda A, Kaszkowiak M, Banach M, et. al. Front Cardiovasc Med. 2021, 8:668653). More importantly, the AF-afflicted individuals with comorbid dehydration, when compared to AF-afflicted individuals without comorbid dehydration, had a sixty and thirty-four percent higher risk of ischemic stroke within ten days following hospital discharge and eleven to twenty days following hospital discharge, respectively. Another study (Swerdel, J, Janevic T, Kostis W et al. Transl Stroke Res. 2017:8: 122-130) described similar data for increased stroke risk 2.3 times greater in AF with dehydration versus AF without dehydration. Chronic dehydration is compounded when an individual experiences acute dehydration due to a fever and infection, especially a respiratory infection which is associated with significant water loss from the lungs. Dehydration may interfere with the efficient functioning of the heart as follows: (1) a decrease in the size of heart cells could alter critical concentrations of essential electrolytes (e.g., Mg, K, Na, and Ca) needed to produce SR; (2) an alteration in the three-dimensional structure of enzymes like the energy-producing Na/K ATPase enzyme, could affect their functionality and interfere in energy production required for heart cells; and (3) an increase in body temperature during vigorous physical activity or from an infection could result in enzyme denaturation, also interfering in energy production for heart cells. Detecting dehydration can be difficult unless one experiences a sense of thirst, excessive sweating, fever, or subjective symptoms like dizziness. According to the U.S. National Academies of Sciences, Engineering, and Medicine, adult males should consume about fifteen and one-half cups (one cup equivalent to eight ounces) of fluids daily, and women approximately eleven and one-half cups daily. This protocol advises a simple, inexpensive method to detect dehydration.

K deficiency is associated with the risk of developing AF (Krijthe B P, Heeringa J, Kors J A, et al. Int J Cardiol. 2013; 168(6):5411-5415), and can occur especially with diuretics, which cause excessive K excretion by the kidneys.

To know whether any treatment protocol effectively converts AF to SR, it is typical to monitor the incidence of AF over a specified time interval, referred to as AF burden. Ideally, this should be done 24/7 with a Holter monitor, but it is expensive and not done as individuals would practically not agree to use this method. Instead, commercially available monitoring APPs can be downloaded on smartphones. They allow the detection of AF and, for example, AF burden can be defined as the number of days of AF occurring per month.

Another method may indirectly monitor the presence and recurrence of AF. It is referred to as HEART RATE VARIABILITY (HRV). HRV is the variation in time between consecutive heartbeats viewed as electrical activity on an EKG. One article (Kim S H, Lim K R, Seo J H, et al. Sci Rep. 2022 Mar. 8; 12:3702) reported reviewing Holter monitor readings on twenty-one hundred individuals, of which seven hundred and eighty-two had hypertension. During a follow-up of about one year, forty-four individuals developed AF. A higher unattenuated (i.e., higher and variable) HRV correlated with occurrences of AF. Another study (Seaborn GEJ, Todd K, Michael K A, et. al. Ann Noninvasive Electrocardiol 2014; 19(1):23-33) reported that HRV may be a prognostic marker for the recurrence of AF after cardiac ablation. All AF-afflicted individuals had unattenuated HRV preoperatively. Those who continued to have unattenuated HRV patterns postoperatively eventually had a recurrence of AF, requiring another catheter ablation procedure. The AF-afflicted individuals with post-operative attenuated HRV did not have recurrences of AF and did not require another catheter ablation procedure. Animal data is often used to support medical applications in humans. One study (Broux B, De Clercq A., Decloedt A. Equine Vet 2017; 49:723-728) on horses observed HRV percentage before and after electrical cardioversion for AF. Unattenuated HRV correlated with the incidence of AF. Conversely, after electrical cardioversion of AF to SR, the HRV was attenuated. As will be described below, the monthly percentage of HRV, when attenuated, parallels the reduced incidence of AF days per month and, as such, maybe a predictor for the recurrence of AF.

SUMMARY

The protocol described in these specifications provides a low-risk, low-cost alternative treatment of AF. It recognizes previously unappreciated facts about Mg and incorporates them into a protocol not currently included in guidelines for the management of AF by the European Society of Cardiology (Hindricks G, Potpara T, Dagres N, et al; Eur Heart J. 202 1; 42:373-498) and the American College of Cardiology (Circulation. 2024; 149: e 1-e156). Current treatment interventions for AF are described as low risk, but their consequences can be serious, even death.

The studies discussed above do not address the other elements of the protocol described herein, namely monitoring K, hydration, encouraging consuming foods high in Mg and K, and the need for frequent daily EKG monitoring. Consequently, there is scientific support and specifications described herein to support this protocol not only can convert AF to SR, prevent the recurrence of AF, but also AF that might occur post-operatively following cardiac surgery and potentially following the successful conversion of AF to SR with conventional therapeutic interventions, such as chemical medications, electrical audio conversion, or cardiac ablation.

An aim of this protocol is to provide a low-cost AF intervention using over-the-counter Mg and K supplements, which may avoid the need for expensive medical treatments.

Another purpose of this invention is to recognize underappreciated or ignored scientific facts required for consistent conversion of AF to SR. These include: (1) Awareness a normal Mg blood level in AF individuals can be misleading because the blood compartment represents only one percent of the total Mg stores in the human body. An AF-afflicted individual with a normal blood Mg level may need Mg supplementation because, coincidentally, they may have low intracellular cardiac concentrations of Mg, needing normalization to convert AF to SR; (2) Another underappreciated fact is the half-life of Mg is six weeks. This fact may explain why short-term (a few days) treatments of AF with Mg sulfate infusions (with a short half-life of twelve hours), have been inconclusive in converting AF to SR. Between six weeks up to 20 or 30 weeks of oral Mg supplements are required to achieve a steady state to maintain the maximal serum concentrations of serum Mg (Zhang X, Gobbo, L C D, Hruby A, et. al. J Nutra. 2016; 146:595-602.).

An objective of this invention is to achieve AF conversion to SR by promoting long-term treatment with optimal Mg supplements (i.e., excellent absorption; capable of achieving rapid blood levels of Mg and maintaining stable 24-hour Mg levels; low gastrointestinal discomfort) in combination with monitoring K requirements, maintaining adequate hydration, consuming foods high in Mg and K content, and frequent EKG interpretations (i.e. ideally daily up to three or four times a day) t o determine the need to titrate doses and/or make changes of Mg formulations.

It is an objective of this invention to provide a low-risk, low-cost alternative therapeutic intervention to convert AF to SR for AF-afflicted individuals who fulfill candidacy for implementation of this protocol.

Additionally, an objective is to prevent recurrences of AF with this protocol and for AF recurrences that might occur following the successful conversion of AF to SR with conventional therapeutic interventions, such as chemical medications, electrical audio conversion, or cardiac ablation and to prevent post-operative AF, especially after cardiac surgery.

Furthermore, it is objective to recognize that the % HRV and AF burden may parallel each other when both are attenuated and that if the % HRV becomes unattenuated, it may be a marker for the recurrence of AF.

BRIEF DESCRIPTIONS OF DRAWING(S)

FIG. 1 is a graph showing the beneficial effects of long-term treatment with oral magnesium supplements, reducing the number of days per month AF was detected. It also shows the effect of oral magnesium supplements on the percentage of heart rate variability (% HRV) per month. It demonstrates that when it and days per month of AF are both attenuated, if the % HRV becomes unattenuated, it can be a marker for the coincidental increase in days of AF per month.

DEFINITIONS

The term "treatment' is used herein to characterize a method that is aimed at (1) converting AF to SR with oral Mg supplements with or without some or all the named elements of the protocol; (2) delaying or preventing the onset or recurrence of AF associated with oral Mg supplements with or without some or all the named elements of the protocol or (3) slowing down or stopping the progression, aggravation, or deterioration of asymptomatic or symptomatic AF with oral Mg supplements and with or without some or all the named elements of the protocol or (4) bringing about amelioration of the symptoms of AF with oral Mg supplements with or without some or all the named elements of the protocol; or (5) curing AF with oral Mg supplements with or without some or all the named elements of the protocol. The treatment may be administered prior to the onset of AF, for a prophylactic or preventive action. It may also be administered after initiation of AF for a therapeutic action to convert AF to SR and conversely to reconvert a recurrence of AF to SR.

The term "Mg" refers to any naturally occurring or non-naturally occurring (i.e., synthetic) compounds containing elemental Mg. The compounds containing Mg can be organic or inorganic compositions and can be manufactured with or without slow-release or long-acting formulations. The compound may be a single molecule, a mixture of two or more molecules, or a complex of at least two molecules. The supplement can have no FDA approval or be approved by the FDA, and similarly not approved or approved by other regulatory agencies, governmental or non-governmental, in the USA or foreign countries. The Mg supplement can have fast absorption in human blood for up to a minimum of three days and can maintain 24-hour blood levels of Mg.

DETAILED DESCRIPTION

The following describes indications and restrictions for individuals considering the implementation of this low-risk, low-cost protocol for converting AF to SR with long-term optimal oral Mg supplement, K supplement, consuming foods high in Mg and K content, maintaining adequate hydration, and frequent EKG monitoring. (1) Candidates must be aware it is elective, requires time for implementation (from six weeks to as long as 20 or 30 weeks), and is not a substitute for conventional interventional therapy when there is an emergency need for AF conversion to SR. (2) This protocol will more likely be effective for asymptomatic persistent AF and long-standing persistent AF and may be less effective if the AF has persisted for many years. In addition, it may not be effective for AF-afflicted individuals who are symptomatic, had recurrences of AF after conventional interventions, or have been refractory to alternative interventions. (3) It requires compatibility with the individual's medical conditions and concurrent medications. It should be avoided in AF-afflicted persons with chronic kidney disease; pregnancy; a history of hypotension (low blood pressure), bradycardia (low heart rate); history of fainting or dizziness as Mg may exacerbate those symptoms; co-existing cardiovascular disease; hyperthyroidism (increased thyroid activity); and other severe or significant co-existing medical conditions. (4) Certain medications may interfere in Mg absorption, for example, proton pump inhibitors, tetracyclines, diuretics, cancer medications, digoxin, and medications that slow gastrointestinal motility because Mg or K supplements may remain longer in the intestine, increasing their absorption and potentially causing toxicity.

The outline of the Zebra Treatment Protocol™ is as follows: (1) Consultation with a HCP is advised for the implementation of this protocol; (2) HCP involvement is required to decide the need for and the continuation of an anticoagulant to decrease the incidence of strokes; (3) Self-monitoring EKGs frequently (i.e., ideally three to four times a day) is advised using commercially available EKG monitoring devices downloaded onto smartphones, such as Apple Watch-iPhone and Kardia. Involvement of a HCP is advised to confirm EKG interpretations; (4) Obtain baseline Mg and other electrolyte blood levels (K, Na, Ca). Baseline tests such as serum creatinine and urine-specific gravity should be included to detect dehydration. All blood tests should be repeated based on HCP recommendations to avoid Mg and/or K toxicity; (5) A cardiac imaging test may be ordered by the HCP, such as a transthoracic echocardiogram (TTE), a transesophageal echogram (TEE) or a special CTA angiogram scan to determine if blood clots exist in the heart, especially in the appendage of the left atrium; (6) Focus maintaining adequate hydration such as with inexpensive methods testing urine specific gravity with a dipstick ideally two to three times weekly. The urine-specific gravity test should be 1.020 or less to confirm adequate hydration; (7) Address predisposing factors for AF; (8) Consume foods high in Mg and K content; (9) Selection of optimal Mg supplements. Ideally, the Mg supplement should have excellent absorption, be a long-acting, slow-release formulation or any formulation to achieve rapid blood levels that are maintained and sustained over repeated twenty-four-hour intervals, capable of normalizing low intracellular cardiac Mg concentrations in AF-afflicted individuals, have minimal gastrointestinal discomfort and is manufactured with quality control. Slow-release and long-acting Mg supplements or any formulation of Mg may satisfy many or all of the ideal characteristics described previously for an oral Mg supplement. Organic Mg supplements are preferred because they have better absorption than inorganic ones, although some inorganic Mg supplements do have good absorption such as Mg chloride. Some common organic Mg supplements include Mg L-Lactate (can be listed as slow-release or not slow-release), Mg gluconate, Mg aspartate, Mg citrate, Mg glycinate, Mg malate, Mg taurate, Mg L-terminate, and Mg glycerophosphate. Avoid supplements that contain more than one ingredient, especially calcium and zinc, which interfere with Mg absorption; (10) K supplementation is necessary if an AF-afflicted individual is on a diuretic. It may also be needed if the conversion of AF doesn't occur because AF may be associated with K deficiency; (11) Continue to monitor heart rhythm with an Apple Watch-iPhone or Kardia or other devices that can obtain and interpret EKGs. (12) Maintain Mg/K doses if SR occurs. However, if SR reverts to AF, increase the Mg supplement slowly and repeat Mg/K blood levels within a few weeks if Mg/K doses or if formulations are changed. The protocol advises titrating the dose of Mg and K based on EKG interpretations, Mg and K blood levels, symptoms of AF, including signs or symptoms of Mg or K toxicity; (13) Maintain oral Mg/K supplements, for example, for at least six weeks up to 20-30 weeks to determine the efficacy of converting AF to SR (supplementation may be administered for less than or more than the example time period). Continue the regimen if the conversion occurs.; (14) If possible, record Heart Rate Variability (% HRV) on a monthly basis (Apple Watch and iPhone record this) because it may correlate with the incidence of AF per month and, as such, is an early detector for AF occurrence. Details on % HRV per month are described further herein.

There are potential risks associated with this treatment protocol as follows: (1) This is an elective protocol and should not be substituted for individuals experiencing AF symptoms requiring immediate intervention with other treatments; (2) AF may not convert to SR using this protocol. (3) During its implementation, because of the extended time needed to determine its efficacy, it is possible that an AF-inflicted individual could experience a spontaneous stroke unrelated to the protocol's implementation.; (4) Regardless of whether one is in SR after converting from AF, the risk of a stroke still can occur compared with someone who has always been in SR; (5) Recurrences of AF are likely to occur with this protocol. (6) Remaining in SR one hundred percent of the time is improbable, so stroke risk may increase during AF recurrences; (6) Toxicity from elevated Mg and/or K blood levels is rare but may occur. Symptoms of elevated Mg include low blood pressure and/or slow heart rate, which may cause dizziness and fainting, fatigue, nausea, vomiting, and muscle weakness. Symptoms of elevated K are muscle fatigue, nausea, weakness, and abnormal heart rhythms that can be life-threatening. Other rare side effects associated with toxic levels of Mg/K may be searched on the internet; (7) Gastrointestinal intolerance with Mg supplements can result in a laxative effect, some more than others, especially inorganic ones, namely Mg oxide and Mg hydroxide; (8) The following is a potential complication that rarely occurs with all AF interventions, including anti-arrhythmic medications, electrical cardioversion, and catheter ablation procedures. It could also occur with this treatment protocol. Conversion of AF to SR could dislodge a clot residing in the heart and cause a stroke. This rare complication may be reduced if a transthoracic echocardiogram or special CTA angiogram of the heart is done to determine if blood clots exist in the heart; (9) Countering this unlikely possibility occurring with this protocol is the realization that not treating AF has an increased risk of a stroke, even on an anti-coagulant.

FIG. 1 is a graph showing the beneficial effects of long-term treatment with oral magnesium supplements, significantly reducing the number of days per month AF was detected. From October 2023 to August 2024, it shows the parallel attenuation of heart rate variability (% HRV) per month and the number of days AF occurred per month. The exception was the month of May 2024, when % HRV was unattenuated compared to the attenuated number of days of AF per month. It occurred when the subject was recovering from a respiratory infection with dehydration from late April to mid-May 2024. The % HRV change from attenuated to unattenuated during that short period correlates with an increase in AF days in April 2024.

The common term to define the incidence of AF is AF burden, the percentage of time a person is in AF during a monitoring period. FIG. 1 is a graph of an example individual's AF burden, defined as the number of days per month with AF. The right side Y-axis 2 represents the number of days of AF per month. The X-axis lists the months from March 2023 to August 2024. Trials with Mg supplements are shown as horizontal lines listing Mg hydroxide, gluconate, and glycinate 4 from April 2023 to March 2024 and Mag-Tab® (Mg L-Lactate SR, a slow-release formulation) 12 from April 2024 to the end of August 2024. The light vertical bar 1 significantly decreased over the twelve months from September 2023 to the end of August 2024, indicating the number of AF days per month in that time interval was 5.8 percent compared to the prior six months from March 2023 to August 2023), which was 20.1 percent. The probability (p) of these results was significant at (p)=0.0143. During the first six-month interval during the administration of Mg supplements 4 (April 2023 to August 2023), there was no consistent reduction in AF until the end of twenty weeks at the end of August 2023. That is consistent with data from study (Zhang X, Gobbo, L C D, Hruby A, et. al. J Nutra. 2016; 146:595-602.) that at least twenty weeks are required to achieve a steady state of maximum blood Mg concentrations. This data is consistent with the long 6-week half-life of Mg in humans.

From September 2023 to the end of August 2024, the incidence of AF per day decreased significantly while on the different Mg supplements 4 and with Mag-Tab® SR (Mg L Lactate SR) 12 from March 2024 to August 2024. The Mag-Tab supplement is a slow-release Mg L-Lactate supplement capable of fast Mg absorption within one hour after taking the dose and maintaining repeat 24-hour Mg blood levels as described in the BACKGROUND. This capability enhanced the continued conversion of AF to SR and has the capacity to reverse a recurrence of AF to SR within one or two days as mentioned in the BACKGROUND.

Holter monitored results are shown as 10,11,13. Monitoring 13 in March 2023 occurred when the AF-afflicted individual experienced AF 39 percent of the time over seven days when no Mg supplements were administered and before the initiation of the protocol described herein. Holter monitoring 10, 11 occurred during Mg supplementation. Holter result 10 was for seven days in December 2023 and detected no AF, although four other days in that month detected AF. Holter result 11 in June 2024 was for fourteen days, and no AF was detected, nor was AF detected on other days of that month.

The months November 2023, January 2024, February 2024, June 2024, May 2024, and August 2024 are marked with an X which is numbered 6, indicating no AF was detected in those months.

During the twelve months from September 2023 to August 2024, three AF recurrences are noted by stars, 7,8, 9. Star 7 was due to K deficiency and reversed to SR by increasing the dose of K. Star 8 was caused by a decrease in dose of Mg and corrected by increasing the Mg dose. Star 9 was caused by dehydration while experiencing a fever and bronchitis and was reversed with hydration. All three AF recurrences reverted to SR for extended periods. There were only 2 days of AF in May 2024, none from June to August 2024, and none after the first week in September 2024, which is not shown on the graph.

The graph also provided data determining whether there was a significant statistical relationship between Heart Rate Variability (HRV) and the number of days of AF per month. The HRV was recorded on an iPhone when the Apple Watch was worn. The HRV represents the time in milliseconds (msec) between two peaks recorded on an EKG. The solid dark vertical bars 3 represent the % HRV % per month. The median % HRV decreased from 110% to 24.1% (p<0.001) from the beginning of six months (March 2023 to August 2023) compared to the subsequent twelve months (September 2023 to August 2024), respectively. Days of AF per month and percent HRV have a moderately strong positive correlation of r=0.670 and a p<0.001. Secondly, the correlation is highly significant when both the % HRV per month and the days per month of AF are attenuated but nearly uncorrelated when both are unattenuated. This indicates when the % HRV becomes unattenuated, it may be a marker for an AF recurrence. There is scientific data to support this correlation, as mentioned in the BACKGROUND.

The invention claimed is:

1. A method to treat an individual with atrial fibrillation (AF) with administration of oral magnesium supplementation for converting AF to sinus rhythm, comprising:
    monitoring cardiac rhythms to determine occurrence of AF;
    administering oral magnesium supplements for a time period configured for AF conversion to sinus rhythm;
    adjusting the magnesium supplements until conversion of AF to sinus rhythm; and
    additional adjusting of the magnesium supplements based upon recurrence of AF, until conversion of AF to sinus rhythm;
    wherein adjusting comprises at least one of titrating a dose of the magnesium supplements and changing a formulation of the magnesium supplements;
    wherein the magnesium supplement is a formulation that exhibits stable twenty-four-hour magnesium blood levels during continuous administration of the magnesium supplement.

2. The method of claim 1, wherein the magnesium supplement is at least one of a slow-release formulation and an extended-release formulation.

3. The method of claim 2 wherein the oral magnesium supplement is absorbed and excreted in the urine, such that it achieves rapid absorption within 1 hour and stable twenty-four hour magnesium blood levels during continuous administration of the magnesium supplement.

4. The method of claim 1 further comprising titrating a dose of potassium until atrial fibrillation conversion to sinus rhythm; and additional titrating the dose of potassium based upon recurrence of atrial fibrillation, until conversion of atrial fibrillation to sinus rhythm.

5. The method of claim 1 wherein hydration status is monitored and corrected based thereon.

15

6. The method of claim 1 wherein the dose of magnesium is titrated based upon magnesium blood level and side effects associated with magnesium.

7. The method of claim 4 wherein the dose of potassium is titrated based upon potassium blood level and side effects associated with potassium.

8. The method of claim 4 wherein a recommended daily allowance for magnesium and potassium is supplemented by consuming foods fortified in potassium and magnesium content.

9. The method of claim 1 observing an attenuated percent of heart rate variability (HRV) with an attenuated incidence of AF for a specified interval of time, and monitoring recurrence of AF.

10. A method to treat an individual with atrial fibrillation (AF) with administration of oral magnesium supplementation for converting AF to sinus rhythm, comprising:

monitoring cardiac rhythms to determine occurrence of AF;

administering oral magnesium supplements for a time period configured for AF conversion to sinus rhythm;

adjusting the magnesium supplements until conversion of AF to sinus rhythm; and additional adjusting the magnesium supplements based upon recurrence of AF, until conversion of AF to sinus rhythm;

wherein adjusting comprises at least one of titrating a dose of the magnesium supplements and changing a formulation of the magnesium supplements; and wherein the magnesium supplement exhibits rapid absorption within 1 hour and stable twenty-four-hour magnesium blood levels during continuous administration of the magnesium supplement.

11. The method of claim 10, wherein the magnesium supplement is at least one of a slow-release formulation and an extended-release formulation.

12. The method of claim 10 wherein the oral magnesium supplement is absorbed and excreted in the urine, such that it achieves a rapid absorption within 1 hour and stable twenty-four hour magnesium blood levels during continuous administration of the magnesium supplement.

13. The method of claim 10 further comprising titrating a dose of potassium until atrial fibrillation conversion to sinus rhythm; and additional titrating the dose of potassium based upon recurrence of atrial fibrillation, until conversion of atrial fibrillation to sinus rhythm.

14. The method of claim 10 wherein hydration status is monitored and corrected based thereon.

15. The method of claim 10 wherein the dose of magnesium is titrated based upon magnesium blood level and side effects associated with magnesium.

16. The method of claim 13 wherein the dose of potassium is titrated based upon potassium blood level and side effects associated with potassium.

17. The method of claim 13 wherein a recommended daily allowance for magnesium and potassium is fortified by consuming foods high in their content.

18. The method of claim 10 observing an attenuated percent of heart rate variability (HRV) with an attenuated incidence of AF for a specified interval of time, and monitoring recurrence of AF.

19. A method to treat an individual with atrial fibrillation (AF) with administration of oral magnesium supplementation for converting AF to sinus rhythm, comprising:

monitoring cardiac rhythms frequently to monitor status of AF and SR;

administering oral magnesium supplements for a time period configured for AF conversion to sinus rhythm;

monitoring hydration status, and correcting hydration status based upon the monitoring; and determining potassium supplementation based upon whether AF has converted to sinus rhythm.

20. The method of claim 19 observing an attenuated percent of heart rate variability (HRV) with an attenuated incidence of AF for an interval of time, and monitoring recurrence of AF.

21. The method of claim 19 wherein the AF comprises asymptomatic persistent or long-standing atrial fibrillation.

22. The method of claim 19 wherein the method is performed to reducing AF recurrence following other treatment interventions that converted AF to sinus rhythm, including at least one of medications, electrical cardioversion, cardiac ablation, and cardiac surgery.

* * * * *